United States Patent [19]
Wagner et al.

[11] Patent Number: 4,855,286
[45] Date of Patent: Aug. 8, 1989

[54] RENIN-INHIBITING DI- AND TRIPEPTIDES, A PROCESS FOR THEIR PREPARATION, AGENTS CONTAINING THEM, AND THEIR USE

[75] Inventors: Adalbert Wagner, Hofheim am Taunus; Heinz-Werner Kleemann, Kelsterbach; Dieter Ruppert; Bernward Schölkens, both of Kelkheim, all of Fed. Rep. of Germany

[73] Assignee: Hoechst Aktiengesellschaft, Frankfurt am Main, Fed. Rep. of Germany

[21] Appl. No.: 78,843

[22] Filed: Jul. 28, 1987

[30] Foreign Application Priority Data

Jul. 30, 1986 [DE] Fed. Rep. of Germany ....... 3625687
Aug. 16, 1986 [DE] Fed. Rep. of Germany ....... 3627877

[51] Int. Cl.$^4$ .................... A61K 37/02; C07D 333/22; C07D 307/02; C07D 209/18; C07C 103/19; C07C 103/00; C07C 103/07; C07C 143/78; C07C 143/74; C07C 125/06

[52] U.S. Cl. .......................... 514/19; 549/76; 549/77; 549/493; 549/494; 548/495; 564/152; 564/154; 564/159; 564/94; 564/95; 560/24; 560/169

[58] Field of Search ............. 530/300, 329, 331, 332, 530/328; 514/17, 11, 16, 19; 548/344, 495; 549/76, 77, 493, 494; 564/152, 154, 159, 94, 95; 560/24, 159

[56] References Cited

U.S. PATENT DOCUMENTS

| | | | |
|---|---|---|---|
| 4,477,440 | 10/1984 | Boger et al. | 530/328 |
| 4,477,441 | 10/1984 | Boger et al. | 530/328 |
| 4,479,941 | 10/1984 | Veber et al. | 514/17 |
| 4,485,099 | 11/1984 | Boger et al. | 514/11 |
| 4,609,641 | 9/1986 | Evans et al. | 514/16 |
| 4,616,088 | 10/1986 | Ryono et al. | 548/344 |
| 4,629,724 | 12/1986 | Ryono et al. | 530/332 |
| 4,636,491 | 1/1987 | Bock et al. | 530/300 |
| 4,661,473 | 4/1987 | Boger et al. | 530/329 |
| 4,663,310 | 5/1987 | Bock et al. | 530/328 |
| 4,665,052 | 5/1987 | Boger | 514/11 |
| 4,665,193 | 5/1987 | Ryono et al. | 548/344 |
| 4,668,663 | 5/1987 | Boger | 530/328 |
| 4,668,770 | 5/1987 | Boger et al. | 530/331 |
| 4,698,329 | 10/1987 | Matsueda et al. | 530/331 |
| 4,705,846 | 11/1987 | Thaisrivongs | 530/328 |
| 4,727,060 | 2/1988 | Buhlmayer et al. | 530/332 |
| 4,743,584 | 5/1988 | Boger | 514/11 |

OTHER PUBLICATIONS

Chem. Abstr., vol. 108 (1988) 132323.
Chem. Abstr., vol. 104 (1986) 88976.
Chem. Abstr., vol. 105 (1986) 227342.
Chem. Abstr., vol. 108 (1988) 38432.
Chem. Abstr., vol. 107 (1987) 193937.
Greenlee, Pharmaceutical Rev., vol. 4, No. 5, pp. 364–374, publ. 1987.
Hanson et al., Biochem. Biophys. Res. Commun., vol. 146, No. 3, pp. 959–963, publ. Aug. 14, 1973.
Kleinert et al., FEBS Lett., vol. 230, No. 1, 2, pp. 38–42, publ. Mar. 1988.
Iizuka et al., J. Med. Chem., vol. 31, No. 4, pp. 701–704, publ. Apr. 1988.
Plattner et al., Biochem. Biophys. Res. Commun., vol. 139, No. 3, pp. 982–990, publ. Sep. 30, 1986.

Primary Examiner—Delbert R. Phillips
Attorney, Agent, or Firm—Finnegan, Henderson, Farabow, Garrett, & Dunner

[57] ABSTRACT

The invention relates to compounds of the formula

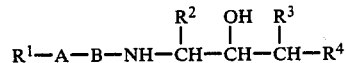

in which $R^1$ is absent or denotes hydrogen, alkyl or acyl, A denotes an acyl radical or an amino acid residue, B denotes an amino acid residue, and $R^2$, $R^3$ and $R^4$ are as defined in the specification, and to their salts, to a process for their preparation, to pharmaceutical products containing them, and to their use as medicaments, and intermediates for the preparation of these compounds.

8 Claims, No Drawings

RENIN-INHIBITING DI- AND TRIPEPTIDES, A PROCESS FOR THEIR PREPARATION, AGENTS CONTAINING THEM, AND THEIR USE

European Patents A-152,255, A-155,809, A-163,237, A-172,346, A-172,347 and A-179,352 disclose di- and tripeptide derivatives and their use as renin inhibitors.

New peptide derivatives which, in vitro and in vivo, are highly active inhibitors of the enzyme renin have been found.

The invention relates to compounds of the formula I

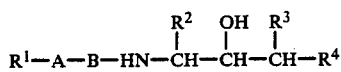

in which $R^1$ ($a_1$) is absent or denotes hydrogen, ($a_2$) denotes ($C_1$–$C_{20}$)-alkyl which is optionally substituted by one, two or three, identical or different radicals from the series comprising hydroxyl, ($C_1$–$C_7$)-alkoxy, ($C_1$–$C_7$)-alkanoyloxy, carboxyl, ($C_1$–$C_7$)-alkoxycarbonyl, ($C_1$–$C_8$)-alkanoyloxy, Cl, Br, amino, ($C_1$–$C_7$)-alkylamino, di-($C_1$–$C_7$)-alkylamino, ($C_1$–$C_5$)-alkoxycarbonylamino or ($C_7$–$C_{11}$)-aralkyloxycarbonylamino, or denotes ($C_3$–$C_8$)-cycloalkyl, ($C_3$–$C_8$)-cycloalkyl-($C_1$–$C_{10}$)-alkyl, or ($C_6$–$C_{14}$)-aryl-($C_1$–$C_8$)-alkyl which is optionally substituted in the aryl moiety by one or two, identical or different radicals from the series comprising F, Cl, Br, hydroxyl, ($C_1$–$C_7$)-alkoxy, ($C_1$–$C_7$)-alkyl, ($C_1$–$C_7$)-alkoxycarbonyl, amino or trifluoromethyl, or ($a_3$) denotes a radical of the formula II

in which W represents —CO—, —O—CO—, —$SO_2$— or —NH—CO—, and $R^a$ represents hydrogen, ($C_1$–$C_{10}$)-alkyl which is optionally singly or doubly unsaturated and which is optionally substituted by up to 3 identical or different radicals from the series comprising hydroxyl, ($C_1$–$C_7$)-alkoxy, ($C_1$–$C_7$)-alkanoyloxy, carboxyl, ($C_1$–$C_7$)-alkoxycarbonyl, Cl, Br, amino, ($C_1$–$C_7$)-alkylamino, di-($C_1$–$C_7$)-alkylamino, ($C_1$–$C_5$)-alkoxycarbonylamino, ($C_7$–$C_{15}$)-aralkoxycarbonylamino and 9-fluoroenylmethoxycarbonylamino, or represents ($C_3$–$C_8$)-cycloalkyl, ($C_3$–$C_8$)-cycloalkyl-($C_1$–$C_6$)-alkyl, $C_6$–$C_{14}$)-aryl which is optionally substituted by one or two identical or different radicals from the series comprising F, Cl, Br, I, hydroxyl, ($C_1$–$C_7$)-alkoxy, ($C_1$–$C_7$)-alkyl, ($C_1$–$C_7$)-alkoxycarbonyl, amino, anilino which is optionally substituted by up to 2 halogens, and trifluoromethyl, or represents ($C_6$–$C_{14}$)-aryl-($C_1$–$C_6$)-alkyl in which the aryl moiety is optionally substituted by one or two identical or different radicals from the series comprising F, Cl, Br, I, hydroxyl, ($C_1$–$C_7$)-alkoxy, ($C_1$–$C_7$)-alkyl, ($C_1$–$C_7$)-alkoxycarbonyl, amino, ($C_1$–$C_7$)-alkylamino, di-($C_1$–$C_7$)-alkylamino, carboxyl, carboxymethoxy, amino($C_1$–$C_7$)-alkyl, ($C_1$–$C_7$)-alkylamino-($C_1$–$C_7$)-alkyl, di-($C_1$–$C_7$)-alkylamino-($C_1$–$C_7$)-alkyl, ($C_1$–$C_7$)-alkoxycarbonylmethoxy, carbamoyl, sulfamoyl, ($C_1$–$C_7$)-alkoxysulfonyl, sulfo- and guanidinomethyl, or represents the radical of a 5- or 6-membered monocyclic, or 9- or 10-membered bicyclic, heteroaromatic compound which has at least 1 carbon atom, 1-4 nitrogen atoms and/or 1 sulfur or oxygen atom, also as ring members, and is optionally mono-, di- or trisubstituted as defined for ($C_6$–$C_{14}$)-aryl under $a_2$), $R^4$ denotes a radical of the formula IV

A ($b_1$) denotes a radical of the formula III

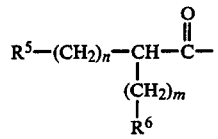

in which n and m are identical or different and denote 0, 1, 2, 3 or 4, $R^5$ and $R^6$ are identical or different and denote phenyl, 2- of 3-thienyl, 2-, 3- or 4-pyridyl, 1-, 2- or 4-imidazolyl, 1- or 2-naphthyl, 2- or 3-benzo[b]thienyl, OH or hydrogen, or ($b_2$) denotes a radical, which is linked N-terminal with $R^1$ and C-terminal with B, of an amino acid from the series comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, β-2-benzo[b]thienylalanine, β-3-benzo[b ]thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyldopa, 2-amino-4-(2-thienyl)butyric acid, 2-amino-4-(3-thienyl)butyric acid, 3-(2-thienyl)serine, norvaline, (Z)-dehydrophenylalanine and (E)-dehydrophenylalanine, B denotes a radical of an amino acid as defined under $b_2$), or $R^4$ denotes a radical of the formula V

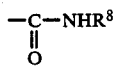

and

A and B are identical or different, and one of the radicals A and B represents a radical of an amino acid from the series comprising β-2-thienylalanine, β-3-thienylalanine, β-2-benzo[b]thienylalanine and β-3-benzo[b]thienylalanine, and the other is as defined above under $b_2$), $R^2$ denotes hydrogen, ($C_1$–$C_{10}$)-alkyl, ($C_4$–$C_7$)-cycloalkyl, ($C_4$–$C_7$)-cycloalkyl-($C_1$–$C_4$)-alkyl, ($C_6$–$C_{14}$)-aryl or ($C_6$–$C_{14}$)-aryl-($C_1$–$C_4$)-alkyl, and $R^3$ denotes hydrogen, ($C_1$–$C_{10}$)-alkyl, ($C_6$–$C_{14}$)-aryl or ($C_6$–$C_{14}$)-aryl-($C_1$–$C_4$)-alkyl, X can be chosen to be absent or denotes O or S, n' can be 0, 1, 2, 3 or 4, $R^7$ denotes hydrogen, OH, $NH_2$, or heteroaryl which can also be partially or completely hydrogenated, or denotes a radical of the formula VI $$-\overset{R^9}{\underset{|}{CH}}-(CH_2)_p-Y-(CH_2)_q-R^{10} \quad (VI)$$

$R^8$ denotes hydrogen, heteroaryl which can also be partially or completely hydrogenated, or a radical of the formula VI, $R^9$ representing hydrogen, $(C_1-C_7)$-alkyl, or $(C_1-C_7)$-alkyl which is monosubstituted by hydroxyl, $(C_1-C_5)$-alkoxy, $(C_1-C_5)$-alkylthio, carboxyl, $(C_1-C_5)$-alkoxycarbonyl, F, Cl, Br, I, $(C_1-C_5)$-alkylamino, di-$(C_1-C_5)$-alkylamino, $(C_1-C_5)$-alkoxycarbonylamino or $(C_7-C_{15})$-aralkoxycarbonylamino, $R^{10}$ denoting OH or $NH_2$, Y being absent or denoting $$-\overset{OH}{\underset{|}{CH}}-,$$

p and q, independently of one another denoting 0, 1, 2, 3 or 4, and in the case where Y is $$-\overset{OH}{\underset{|}{CH}}-,$$

q not being equal to 0, and heteroaryl denoting the radical of a heteroaromatic compound defined under (a₃), and to their physiologically tolerated salts.

The carbon atoms substituted by $R^2$, hydroxyl and $R^3$ can each have the R, S or R,S-configuration.

Alkyl can be straight-chain or branched. A corresponding statement applies to radicals derived therefrom, such as, for example, alkoxy, alklthio, alkylamino, dialkylamino, alkanoyl and aralkyl.

Cycloalkyl is to be understood to include alkyl-substituted radicals, such as, for example, 4-methylcyclohexyl or 2,3-dimethylcyclopentyl. Examples of $(C_6-C_{14})$-aryl are phenyl, naphthyl, biphenyl-yl or fluorenyl; phenyl is preferred. A corresponding statement applies to radicals derived therefrom, such as, for example, aryloxy, aroyl, aralkyl and aralkyloxy. Aralkyl is to be understood to be an unsubstituted or substituted $(C_6-C_{14})$-aryl radical which is linked to $(C_1-C_6)$-alkyl, such as, for example, benzyl, α- and β-naphthylmethyl, halobenzyl and alkoxybenzyl, without aralkyl being, however, restricted to the radicals mentioned.

A radical of a 5- or 6-membered monocyclic, or 9- or 10-membered bicyclic, heteroaromatic compound which has at least 1 carbon atom, 1-4 nitrogen atoms and/or 1 sulfur or oxygen atom as ring members is understood to comprise radicals of heteroaromatic compounds as are defined, for example, in Katritzky, Lagowski, Chemistry of Heterocyclic Compounds, Berlin, Heidelberg 1968, pages 3-5. The radical of a heteroaromatic compound can be substituted by one, two or three, preferably one or two, identical or different radicals from the series comprising F, Cl, Br, hydroxyl, $(C_1-C_7)$-alkoxy, $(C_1-C_7)$-alkyl, $(C_1-C_7)$-alkoxycarbonyl, amino or trifluoromethyl. Examples of monocyclic heteroaromatic compounds are thiophene, furan, pyrrole, imidazole, pyrazole, pyridine, pyrazine, pyrimididine, pyridazine, 1,2,4-triazole, thiazole, tetrazole, isothiazole, oxazole and isoxazole. Examples of bicyclic heteroaromatic compounds are benzothiophene, benzofuran, indole, isoindole, indazole, benzimidazole, quinoline, isoquinoline, phthalazine, quinoxaline, quinazoline and cinnoline. A corresponding statement applies to heteroaryl-derived radicals such as, for example, completely or partially hydrogenated heteroaryl, heteroaryloxy, heteroaryl and heteroarylalkyl.

The amino acids A and B in formula I are linked together by an amide bond and are natural or unnatural α-amino acids of the L, D or D,L configuration, preferably of the L configuration. A corresponding statement applies to amino acids or their derivatives as radicals $R^4$.

Salts of compounds of the formula I are particularly to be understood to be pharmaceutically utilizable or non-toxic salts.

Salts of these types are formed, for example, from compounds of the formula I which contain acidic groups, for example carboxyl, with alkali metals or alkaline earth metals, such as Na, K, Mg and Ca, and with physiologically tolerated organic amines such as, for example, triethylamine and tri(2-hydroxyethyl)amine.

Compounds of the formula I which contain basic groups, for example an amino group or a guanidino group, form salts with inorganic acids such as, for example, hydrochloric acid, sulfuric acid or phosphoric acid, and with organic carboxylic or sulfonic acids such as, for example, acetic acid, citric acid, benzoic acid, maleic acid, fumaric acid, tartaric acid and p-toluenesulfonic acid.

Preferred compounds of the formula I are those in which the radicals are defined as follows:

$R^1$ is preferably absent, denotes hydrogen or represents $(C_1-C_{10})$-alkyl, cyclopentyl, cyclohexyl, cyclopentyl-$(C_1-C_{10})$-alkyl, cyclohexyl-$(C_1-C_{10})$-alkyl, optionally substituted phenyl-$(C_1-C_8)$-alkyl, $H_2N$-$(C_1-C_{10})$-alkyl, HO-$(C_1-C_{10})$-alkyl, $(C_1-C_4)$-alkoxy-$(C_1-C_{10})$-alkyl, $(C_1-C_4)$-alkoxycarbonyl-$(C_1-C_{10})$-alkyl, carboxy-$(C_1-C_{10})$-alkyl such as 2-hydroxypropionyl or 2-hydroxy-3-methylbutyryl, $(C_1-C_8)$-alkanoyloxy-$(C_1-C_{10})$-alkyl, $(C_1-C_{11})$-alkanoyl such as n-decanoyl, formyl, acetyl, pivaloyl, isovaleryl or isobutyryl, optionally protected amino-$(C_2-C_{11})$-alkanoyl such as 4-aminobutyryl, 5-aminopentanoyl, 6-aminohexanoyl, 4-N-tert.-butoxycarbonylaminobutyryl, 5-N-tert.-butoxycarbonylaminopentanoyl or 6-N-tert.-butoxycarbonylaminohexanoyl, di-$(C_1-C_7)$-alkylamino-$(C_2-C_{11})$-alkanoyl such as dimethylaminoacetyl, $(C_4-C_9)$-cycloalkylcarbonyl such as cyclopropylcarbonyl, cyclobutylcarbonyl, cyclopentylcarbonyl or cyclohexylcarbonyl, $(C_6-C_{10})$-aryl-$(C_2-C_{11})$-alkanoyl such as phenylacetyl, phenylpropanol or phenylbutanoyl, 2-(2,6-dichloroanilino)phenylacetyl, 2-(N-benzyl-2,6-dichloroanilino)phenylacetyl, benzoyl which is optionally substituted by halogen, $(C_1-C_7)$-alkyl, $(C_1-C_7)$-alkoxy or $(C_1-C_7)$-alkoxycarbonyl, such as 4-chlorobenzoyl, 4-methylbenzoyl, 2-methoxycarbonylbenzoyl or 4-methoxybenzoyl, 2-pyrrolylcarbonyl, 3-pyridylcarbonyl, benzenesulfonyl, $(C_1-C_{10})$-alkoxycarbonyl such as methoxycarbonyl, ethoxycarbonyl or tert.-butoxycarbonyl, $(C_1-C_{10})$-alkoxycarbonyl which is substituted by halogen, such as 2,2,2-trichloroethoxycarbonyl or 1,1-dimethyl-2,2,2-trichloroethoxycarbonyl, $(C_6-C_{14})$-aryl-$(C_1-C_6)$-alkoxycarbonyl such as benzyloxycarbonyl or 9-fluorenylmethylcarbonyl.

$R^2$ is preferably isobutyl, benzyl or cyclohexylmethyl, $R^3$ is preferably hydrogen, isopropyl or isobutyl, $R^4$ is preferably as defined above, $R^{10}$ denoting, however, NH$_2$, or represents optionally substituted heteroaryl which is as defined above but has 1 or 2 nitrogen atoms.

$R^5$ and $R^6$ are identical or different and preferably represent phenyl, 2-thienyl, 2-pyridyl, 1-naphthyl, 2-benzo[b]thienyl, 3-benzo[b]thienyl, OH or hydrogen, and n', p and q preferably represent 0 or 1.

Preferred amino acids which are suitable for the radicals A and B are phenylalanine, histidine, tyrosine, tryptophan, methionine, leucine, isoleucine, asparagine, aspartic acid, β-2-thienylalanine, β-3-thienylalanine, lysine, ornithine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norleucine, valine, alanine, 1,2,3,4-tetrahydroisoquinoline-3-carboxylic acid, homophenylalanine, 2-amino-4-(2-thienyl)butyric acid, (Z)-dehydrophenylalanine, norvaline, β-2-furylalanine or (E)-dehydrophenylalanine. In addition, A preferably denotes a radical of the formula III as described under (b$_1$).

The invention also relates to a process for the preparation of compounds of the formula I, which comprises coupling a fragment having a terminal carboxyl group, or its reactive derivative, with an appropriate fragment having a free amino group, where appropriate elimination of (a) protective group(s) temporarily introduced to protect other functional groups, and, where appropriate, conversion of the resulting compound into its physiologically tolerated salt.

Fragments of a compound of the formula I having a terminal carboxyl group have the formulae VII a-VII d which follow:

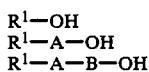 (VIIa)
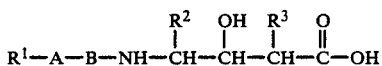 (VIIb)

R$^1$—OH (VIIa)
R$^1$—A—OH (VIIb)
R$^1$—A—B—OH (VIIc)

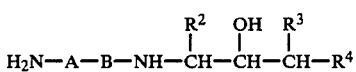 (VIId)

Fragments of a compound of the formula I having a terminal amino group have the formulae VIII a-VIII d which follow:

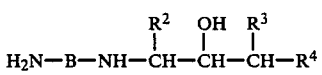 (VIIIa)

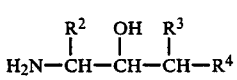 (VIIIb)

 (VIIIc)

NH$_2$—R$^8$ (VIIId)

Methods suitable for the preparation of an amide bond are described in, for example, Houben-Weyl, Methoden der organischen Chemie (Methods of Organic Chemistry), Volume 15/2; Bodanszky et al., Peptide synthesis, 2nd ed. (Wiley & Sons, New York 1976) or Gross, Meienhofer, The Peptides. Analysis, synthesis, biology (Academic Press, New York 1979). The following methods are preferably used: the active ester method with N-hydroxysuccinimide as ester component, coupling with a carbodiimide such as dicyclohexylcarbodiimide, or with propanephosphonic anhydride, and the mixed anhydride method using pivaloyl chloride.

The optically active amines of the formula IX

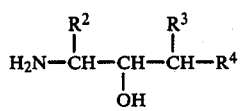 (IX)

which are used as starting compounds and in which R$^2$, R$^3$ and R$^4$ are as defined above are prepared starting from optically active α-amino acids, whose center of asymmetry is retained. For this purpose, an N-protected aldehyde of an amino acid is prepared in a known manner and is coupled, in an aldol-analogous addition, to an appropriate heteroarylalkyl synthon, resulting in amino alcohols of the formula IX after elimination of the N-protective group. Mixtures of compounds diastereomeric at the OH-carrying center are obtained and are separated in a manner known per se, for example by fractional crystallization or by chromatography. The diastereomeric purity is checked by HPLC, and the enantiomeric purity can be checked in a known manner by conversion into Mosher derivatives (H. S. Mosher et al., J. org. Chem. 34, 2543 (1969)). N-Protected aldehydes of amino acids are prepared by the method of B. Castro et al. (Synthesis 1983, 676).

The aldol-analogous addition to N-protected aldehydes of amino acids (preferably N-tert.-butoxycarbonyl and benzyloxycarbonyl protective groups) is carried out in a solvent which is inert to bases, such as ether, THF, toluene, DMF, DMSO or dimethoxyethane.

The bases which can be used for the deprotonation of the heteroarylalkyl component are alkali metal alcoholates such as potassium tert.-butylate and sodium methylate, alkali metal hydrides such as sodium or potassium hydride, organometallic bases such as n-butyllithuum, s-butyllithium, methyllithium or phenyllithium, sodamide and alkali metal salts of organic nitrogen bases, such as lithium diisopropylamide.

The substituted 4-amino-3-hydroxybutyric acids which are contained in the compounds of the general formula I, according to the invention, in which R$^4$ is defined as a radical of the formula V are known from the literature and are prepared by the metho of D. H. Rich et al., J. Org. Chem. 43, 3624 (1978).

The diamines mentioned in the formula V, in which Y is absent, are prepared starting from the optically active α-amino acids, with retention of their center of asymmetry. The conversion of the protected amino acids via the amides into the nitriles is known from the literature, and the subsequent reaction to give the amine can be carried out catalytically, for example with Raney nickel, is a suitable atmosphere of hydrogen.

The diamines mentioned in formula V, with Y=

are obtained from the N-protected aldehydes of amino acids by aldol-analogous addition of, for example, nitromethane and subsequent catalytic hydrogenation, for example in the presence of a transition metal catalyst such as Raney nickel.

It is also possible to check the enantiomeric purity of the diamines of the formula V in a known manner by conversion into Mosher derivatives. The preceding and subsequent operations necessary for the preparation of compounds of the formula I, such as introduction and elimination of protective groups, are known from the literature and described in, for example, T. W. Greene, "Protective Groups in Organic Synthesis". Salts of compounds of the formula I with salt-forming groups are prepared in a manner known per se, for example by reacting a compound of the formula I having a basic group with a stoichiometric amount of a suitable acid. Mixtures of stereoisomers, in particular mixtures of diastereomers which are obtained when racemic amino acids A or B are used, can undergo separation in a manner known per se, by fractional crystallization or by chromatography.

The compounds of the formula I, according to the invention, have enzyme-inhibiting properties; in particular, they inhibit the action of the natural enzyme renin. Renin is a proteolytic enzyme which belongs to the class of aspartyl proteases and is, following various stimuli (volume depletion, sodium deficiency, $\beta$-receptor stimulation), secreted from the juxtaglomerular cells of the kidney into the blood circulation. There it eliminates the decapaptide angiotensin 1 fron the angiotensinogen which is excreted from the liver. Angiotensin 1 is converted by angiotensin converting enzyme (ACE) into angiotensin 2. Angiotensin 2 plays an essential part of the regulation of blood pressure because it directly increases blood pressure by vascular contraction. In addition, it stimulates the secretion of aldosterone fromt he adrenal and, in this way, via inhibition of sodium excretion, increases the extracellular fluid volume, which in turn contributes to an increase in blood pressure. Inhibitors of the enzymatic activity of renin bring about a reduction in the formation of angiotenssin 1 with, as a consequence, a reduction in the formation of angiotensin 2. The decrease in the concentration of this active peptide hormone is the direct cause of the blood pressure-lowering action of renin inhibitors.

The activity of renin inhibitors can be checked by in vitro tests. These entail the reduction in the formation of angiotensin 1 being measured in arious systems (human plasma, procine renin). For this purpose, for example human plasma which contains both renin and angiotensinogen, is incubated at 37° C. with the compound which is to be tested. Subsequently, the concentration of the antiotensin 1 which ha formed during the incubation is measured using a radioimmunoassay. The compounds of the general formula I described in the present invention show, in the in vitro tests used, inhibitory action at concentrations from about $10^{-5}$ to $10 \text{nhu} -10$ mol/l.

Renin inhibitors bring about a reduction in blood pressure in animals which have been depleted of salt. Since human renin differs from the renin of other species, primates (marmosets, rhesus monkeys) are used for the in vivo test of renin inhibitors. Primate renin and human renin are substantially homologous in their sequence. Endogenous release of renin is stimulated by i.v. injection of furosemide. Substantially, the test compounds are administered by continuous infusion, and their action on blood pressure and heart rate is measured. The compounds of the present invention are active in this test in a dose range of about 0.1–5 mg/kg i.v.. The compounds of the general formula I which are described in the present invention can be used as antihypertensives and for the treatment of heart failure.

Thus the invention also relates to the use of compounds of the formula I as medicines and to pharmaceutical products which contain these compounds. Administration to primates, especially to humans, is preferred. Pharmaceutical products contain an effective amount of the active compound of the formula I, together with an inorganic or organic pharmaceutically utilizable vehicle. Administration can be effected intranasally, intravenously, subcutaneously or orally. The dosage of the active compound depends on the species of warm-blooded animal, the body weight, the age and the mode of administration.

The pharmaceutical products of the present invention are prepared in dissolution, mixing, granulating or tablet-coating processes which are known per se.

For a form for oral administration, the active compounds are mixed with the additives customary for this purpose, such as vehicles, stabilizers or inert diluents, and converted by customary methods into suitable forms for administration, such as tablets, coated tablets, hard gelatin capsules, aqueous, alcoholic or oily suspensions or aqueous, alconholic or oily solutions. Examples of inert excipient which can be used are gum arabic, magnesia, magnesia carbonate, potassium phosphate, lactose, glucose, magnesium stearyl fumarate or atarch, especially corn starch. This preparation can be effected as both dry and moist granules. Examples of suitable oily vehicles or solvents are vegetable or animal oils, such as sunflower oil and fish liver oil.

For subcutaneous or intravenous administration, the active compounds, or their physiologically tolerated salts, are converted into solutions, suspensions or emulsions, if desired with the substances customary for this purpose, such as solubilizers, emulsifiers or other auxiliaries. Examples of suitable solvents are: water, physiological saline solutions or alconols, for example ethanol, propanediol of glycerol, as well as sugar solutions such as glucose or mannitol solutions, or a mixture of the various solents mentioned.

List of abbreviations used

| | |
|---|---|
| Ac | acetyl |
| ACHPA | [3S,4S]—4-amino-3-hydroxy-5-cyclohexyl-pentanoic acid |
| BOC | tert.-butoxycarbonyl |
| TLC | thin-layer chromatography |
| DCC | dicyclohexylcarbodiimide |
| DNP | 2,4-dinitrophenyl |
| DMF | dimethylformamide |
| DMSO | dimethyl sulfoxide |
| EA | ethyl acetate |
| Etoc | ethoxycarbonyl |
| FAB | fast atom bombardment |
| H | hexane |
| HOBt | 1-hydroxybenzotriazole |
| Iva | isovaleryl |
| M | molecular peak |
| MeOH | methanol |
| MS | mass spectrum |
| MTB | methyl tert.-butyl ether |
| R.T. | room temperature |
| m.p. | melting point |
| Sta | [3S,4S]—4-amino-3-hydroxy-6-methylheptanoic acid |
| Thi | $\beta$-2-thienylalanine |

| | |
|---|---|
| THF | tetrahydrofuran |
| Z | benzyloxycarbonyl |

The other abbreviations which are used for amino acids correspond to the three-letter code which is customary in peptide chemistry and is described, for example, in Europ. J. Biochem. 138, 9–37 (1984). Unless expressly indicated otherwise, the amino acids always have the L configuration.

The designation "R" such as, for example, in

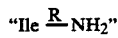

represents an amide bond in which the carbonyl group has been replaced by a methylene group.

The Examples which follow serve to illustrate the present invention without intending to restrict it to them.

REFERENCE EXAMPLE 1

Boc—Phe—His—ACHPA—Leu $\underline{R}$ NH$_2$:

80 mg of

dissolved in 10 ml of methanol, are hydrogenated with H$_2$ under atmospheric pressure and with 50 mg Pd on active charcoal (10%) as catalyst. After 6 h at R.T., the catalyst is removed by filtration through kieselguhr. The filtrate is concentrated and freeze-dried, resulting in a colorless powder.

R$_f$=(EA/methanol 1:1)=0.15; MS (FAB): 698 (M+1).

 (a)

230 mg of

in 5 ml of DMF are stirred with 0.5 ml of thiophenol at R.T. for 3 h. The mixture is concentrated in vacuo, and the residue is digested 3 times with diisopropyl ether. Chromatography on silica gel (mobile phase EA/methanol 15:1) and concentration of the fractions containing the product result in a colorless powder.

R$_f$(EA/MeOH 5:1)=0.5; MS (FAB): 832 (M+1).

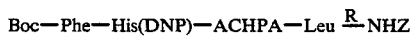 (b)

44 μl of pivaloyl chloride are added, at −5° C., to 192 mg of Boc—Phe—His(DNP)—OH, 30 μl of pyridine and 50 μl of N-ethylpiperidine in 10 ml of CH$_2$Cl$_2$. The mixture is stirred at +5 to +10° C. for A30 min, cooled to −10° C., and 165 mg of

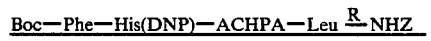

in 5 ml of CH$_2$Cl$_2$ are added dropwise. The mixture is stirred without cooling for 16 h and is concentrated in vacuo, and the residue is taken up in 100 ml of EA. The solution is extracted 3 times with aqueous K$_2$CO$_3$ solution and once with H$_2$O, dried over Na$_2$SO$_4$ and concentrated in vacuo. Chromatography on silica gel (mobile phase EA/methanol (10:1) results in the title compound as a pale yellowish powder.

R$_f$(EA/methanol 10:1)=0.5; MS (FAB): 998 (M+1)

 (c)

200 mg of

are dissolved in 5 ml of dioxane. While cooling slightly (+10° C.), 10 ml of 12% strength HCl in dioxane are added. After 3 h at R.T., the mixture is concentrated in vacuo, the residue is taken up in H$_2$O, and the solution is adjusted to pH 9–10 with saturated aqueous Na$_2$CO$_3$ solution and extracted 3 times with EA. Drying with Na$_2$SO$_4$ and concentration in vacuo result in the title compound which can be used without further purification in the subsequent coupling steps.

(d) Boc—Phe—His(DNP)—OH is prepared from Boc—Phe—O—N—Suc and H—His(DNP)—OH by the active ester method (J. Amer. Chem. Soc. 86 [1964] 1839).

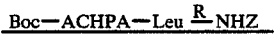 (e)

180 mg of DCC dissolved in 5 ml of THF are added dropwise, at 0° C., to 250 mg of Boc—ACHPA—OH (preparation given in J. Med. Chem. 28 [1985], 1779) and 160 mg of HOBt in 10 ml of THF. After 1 h without cooling, 279 mg of

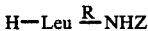

in 10 ml of THF are added at 0° C. After 16 h at R.T., the mixture is filtered, the filtrate is concentrated, and the residue is dissolved in EA. The solution is extracted twice with saturated aqueous Na$_2$CO$_3$ solution and once with H$_2$O. After drying with Na$_2$SO$_4$, the solution is concentrated. Chromatography on silica gel (mobile phase EA/n-hexane 2:1) results in the title compound as a colorless powder.

R$_f$(EA/n-hexane)=0.7; MS (FAB): 548 (M+1).

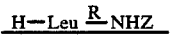 (f)

In analogy to reference example 1(c) and starting from 350 mg of

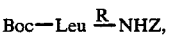

the title compound is obtained as a foam which is used without further purification for the subsequent coupling.

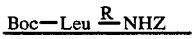 (g)

600 mg of

and 693 mg of Z—O—succinimide dissolved in 10 ml of DMF are stirred at R.T. for 16 h. The mixture is concentrated in vacuo, the residue is dissolved in EA, and the solution is extracted twice with saturated aqueous NaCl solution, twice with saturated aqueous KHSO$_4$ solution and once with saturated aqueous NaCl solution. Concentration in vacuo results in the title compound as a colorless oil which is used further without further purification.

R$_f$(EA)=0.8; MS (FAB): 351 (M+1).

 (h)

2.8 g of Boc—Leu-nitrile (preparation analogous to J. Amer. Chem. Soc. 88 (1966), 2033) are hydrogenated with pretreated Raney Ni (pretreatment: (1) thoroughly washed with H$_2$O, (2) heated with decalin and decanted, (3) suspended in methanol and decanted) in 100 ml of dilute ammoniacal methanol at R.T. for 2 h. After filtration and concentration in vacuo, the pH is adjusted to 2 with aqueous 2N citric acid, and the mixture is extracted 3 times with CH$_2$Cl$_2$. The aqueous phase is adjusted to pH 8-9 with aqueous 2N NaOH solution and then extracted 3 more times with CH$_2$Cl$_2$. The combined organic extracts are washed once with H$_2$O, dried with Na$_2$SO$_4$ and concentrated. The pale yellow oil can be used without further purification for the subsequent reactions.

R$_f$(methanol/1% NH$_3$)=0.6; MS: 217 (M+1).

EXAMPLE 1

280 mg of

are dissolved in 3 ml of 33% strength HBr solution in glacial acetic acid, and the solution is stirred at R.T. for 3 h. 50 ml of saturated aqueous Na$_2$CO$_3$ are added, the mixture is extracted twice with 50 ml of EA each time, and the organic phase is dried over Na$_2$SO$_4$. Chromatography on silica gel (methanol) provides the title compound as a colorless oil.

R$_f$(MeOH)=0.08; MS (FAB): 676 (M+1).

(a) 

475 mg of

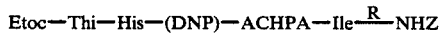

are reacted in analogy to reference example 1(a) with thiophenol to give the title compound.

R$_f$(EA/MeOH 8:1)=0.20; MS (FAB): (M+1).

(b) 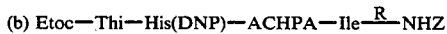

380 mg of

are dissolved in 2 ml of dioxane, and 9 ml of half-concentrated HCl in dioxane are added. The mixture is stirred at R.T. for 3 h, the dioxane is removed in vacuo, the residue is taken up in 50 ml of EA/50 ml of saturated aqueous NaHCO$_3$, and the aqueous phase is extracted twice more with 50 ml of EA. The organic phase is dried over Na$_2$SO$_4$ and concentrated in vacuo. The residue is taken up in 5 ml of THF, and the solution is stirred with 104 mg of Etoc—Thi—OH, 97 mg of DCC and 86 mg of HOBt at R.T. for 15 h. The dicyclohexylurea is filtered off, the filtrate is concentrated in vacuo, and the residue is taken up in 50 ml of EA. The solution is extracted twice with 50 ml of saturated aqueous NaHCO$_3$ solution and once with H$_2$O, dried over Na$_2$SO$_4$ and concentrated in vacuo. The title compound is obtained as a yellow oil which is reacted further without purification.

R$_f$(EA/MeOH 5:1)=0.61.

(c) 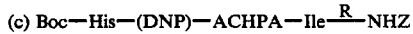

0.37 ml of pivaloyl chloride is added, at −5° c., to 1.34 g of Boc—His(DNP)—OH, 0.26 ml of pyridine and 0.46 ml of N-ethylpiperidine in 100 ml of CH$_2$Cl$_2$. The mixture is stirred at +5° to +10° C. for 30 min, cooled to −10° C., and 1.32 g of

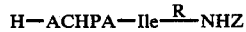

in 50 ml of CH$_2$Cl$_2$ are added dropwise. The mixture is stirred without cooling for 16 h. concentrated in vacuo, and the residue is taken up in 300 ml of EA. The solution is extracted once with 100 ml of K$_2$CO$_3$ solution and water in each case, dried over Na$_2$SO$_4$ and concentrated in vacuo. Chromatography on silica gel (mobile phase MTB) results in the title compound as a pale yellowish powder.

R$_f$(MTB)=0.1; MS (FAB): 851 (M+1).

(d) 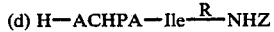

1.50 g of

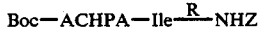

are dissolved in 25 ml of dioxane. 55 ml of 12% strength HCl in dioxane are added at 0° C. After 4 h at R.T., the mixture is concentrated in vacuo, the residue is taken up in H$_2$O, the pH is adjusted to 9-10 with saturated aqueous Na$_2$CO$_3$ solution, and the solution is extracted 3 times with 100 ml of EA. Drying with Na$_2$SO$_4$ and concentration in vacuo results in the title compound which can be used without further purification in the subsequent coupling steps.

 (e)

1.8 g of DCC dissolved in 50 ml of THF are added drowise, at 0° C., to 2.5 g of Boc—ACHPA—OH (preparation as given in J. Med. Chem. 28 (1985), 1779)

and 1.6 g of HOBt in 100 ml of THF. After 1 h without cooling, 2.8 g of

in 100 ml of THF are added at 0° C. After 16 h at R.T., the mixture is filtered, the filtrate is concentrated, and the residue is dissolved in 100 ml of EA. The solution is extracted twice with 50 ml of Na₂CO₃ solution each time, and once with 50 ml of H₂O. It is dried over Na₂SO₄ and concentrated in vacuo, and the residue is chromatographed on silica gel (mobile phase EA/n-hexane 1:1). The title compound is obtained as a colorless powder.

$R_f$(EA/n-hexane 1:1)=0.2; MS (FAB): 548 (M+1).

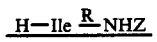 (f)

In analogy to Example 1(d) and starting from 3.5 g of

the title compound is obtained as a foam which is used without further purification for the subsequent coupling.

 (g)

6.0 g of

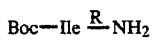

and 6.9 g of Z—O—succinimide dissolved in 100 ml of DMF are stirred at R.T. for 16 h. After concentration in vacuo, the residue is dissolved in 100 ml of EA, and the solution is extracted twice with 100 ml of saturated aqueous KHSO₄ solution. Drying over Na₂SO₄ and concentration in vacuo results in the title compound as a colorless oil which is used further without purification.

$R_f$(EA)=0.8; MS (FAB): 351 (M+1).

(h) 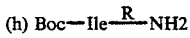

28.0 g of Boc—L—2-amino-3-methylvaeronitrile (preparation in analogy to J. Amer. Chem. Soc. 88 (1966), 2033) are hydrogenated with pretreated Raney Ni (treatment: (1) thoroughly washed with H₂O, (2) heated with decalin and decanted, (3) suspended in methanol and decanted) in 1 L of dilute NH₃ in methanol at R.T. for 2 h. After filtration and concentration in vacuo, the residue is taken up in 500 ml of EA, and the solution is extracted 3 times with 200 ml of 5% aqueous NaHSO₄ solution. The aqueous phase is now adjusted to pH 9 with 2N NaOH solution and is extracted 3 times with 200 ml of EA. The organic phase is dried over Na₂SO₄, and the solvent is removed in vacuo. The pale yellow oil can be reacted further without further purification.

$R_f$(MeOH/1% NH₃)=0.6; MS: 217 (M+1).

The compounds of Examples 2-4 are prepared in analogy to Example 1.

EXAMPLE 2

$R_f$(EA/MeOH 1:1)=0.1; MS (FAB): 688 (M+1).

EXAMPLE 3

$R_f$(MeOH)=0.08; MS (FAB): 676 (M+1)

EXAMPLE 4

$R_f$(EA/MeOH 1:1)=0.1; MS (FAB): 688 (M+1).

EXAMPLE 5

Iva-Phe-His-1(S)-cyclohexylmethyl-2(S),4-dihydroxybutylamide 310 mg of Iva-Phe-His(DNP)-cyclohexylmethyl-2(S),4-dihydroxybutylamide are reacted with thiophenol to give the title compound in analogy to reference example 1a.

$R_f$ (acetonitrile/water 10:1)=0.20; MS (FAB): 570 (M+1).

(a)
Iva-Phe-His(DNP)-cyclohexylmethyl-2(S),4-dihydroxybutylamide

In analogy to reference example 1(b), 657 mg of Iva—Phe—His(DNP)—OH and 360 mg of 1(S)-cyclohexylmethyl-2(S),4-dihydroxybutylamine are coupled with pivaloyl chloride.

$R_f$E (EA/MeOH 10:1)=0.45; MS (FAB): 736 (M+1).

(b)
1(S)-Cyclohexylmethyl-2(S),4-dihydroxybutylamine

In analogy to reference example 1(c), the protective group is removed from 620 mg of N-Boc-1(S)-cyclohexylmethyl-2(S),4-dihydroxybutylamine using HCl/dioxane.

$R_f$(MeOH)=0.13;

(c)
N-Boc-1(S)-cyclohexylmethyl-2(S),4-dihydroxybutylamine

A total of 0.17 g of LiAlH₄ in small portions is added, at 0° C., to 1.0 g of Boc-ACHPA-OEt [preparation as given in J. Med. Chem. 28, (1985) 1779] in 50 ml of THF under argon, and the mixture is stirred at R.T. for 2 h. 0.90 g of KHSO₄ in 20 ml of H₂O are added dropwise, the THF is removed in vacuo, and the residue is extracted 3 times with 20 ml of CH₂Cl₂ each time. After drying over Na₂SO₄ and concentration in vacuo, the residue is chromatographed on silica gel (mobile phase MTB/cyclohexane 1:1), and the title compound is obtained as colorless crystals.

Melting point 77°-79° C.;

$R_f$ (MTB/cyclohexane 1:1)=0.11; MS (FAB): 302 (M+1)

(d)

Iva—Phe—His (DNP)—OH is prepared from Iva—Phe—ONSuc and H—His(DNP)—OH by the active ester method (J. Amer. Chem. Soc. 86 [1964] 1839).

EXAMPLE 6

Iva-Phe-His-1(S)-cyclohexylmethyl-2(R,S)-hydroxy-3-(2-pyridyl)propylamide 380 mg of Iva-Phe-His(DNP)-1(S)-cyclohexylmethyl-2(R,S)-hydroxy-3-(2-pyridyl)propylamide are reacted with thiophenol to give the title compound in analogy to reference example 1(a).

$R_f$(EA/methanol 5:1)=0.15; MS (FAB): 617 (M+1).

(a)

Iva-Phe-His(DNP)-1(S)-cyclohexylmethyl-2(R,S)-hydroxy-3-(2-pyridyl)propylamide 610 mg of Iva—Phe—His(DNP)—OH and 300 mg of 1(S)-cyclohexylmethyl-2(R,S)-hydroxy-3-(2-pyridyl)-propylamine are reacted by the pivaloyl chloride method to give the title compound in analogy to reference example 1(b).

$R_f$(EA/methanol 10:1)=0.3; MS (FAB): 783 (M+1).

(b)

1(S)-Cyclohexylmethyl-2(R,S)-hydroxy-3-(2-pyridyl)-propylamine 400 mg of Boc-[1(S)-cyclohexylmethyl-2(R,S)-hydroxy-3-(2-pyridyl)]propylamine are reacted with dioxane/HCl to give the title compound in analogy to reference example 1(c).

(c)

Boc[1(S)-Cyclohexylmethyl-2(R,S)-hydroxy-3-(2-pyridyl)]propylamine 13 ml of n-butyllithium (15% in hexane) are added, at −30° C., to 2 ml of 2-methylpyridine dissolved in 20 ml of THF. The mixture is stirred without cooling for 1 h, and then at 10° C. 2.55 g of Boc-cyclohexylalaninal in 25 ml of THF are added dropwise. 10 ml of H$_2$O are added immediately thereafter. The mixture is now extracted 3 times with EA, and the extracts are dried with Na$_2$SO$_4$ and concentrated in vacuo. Chromatography on silica gel (mobile phase EA/n-hexane 1:1) provides the title compound as a yellowish oil, with the diastereomers being obtained separately. (This also applies to all analogous examples).

$R_f$(EA/n-hexane) = 0.15 (polar diastereomer)
= 0.25 (less polar diastereomer)

MS: 349 (M+1).

EXAMPLE 7

Iva-Phe-His-1(S)-cyclohexylmethyl-2(R,S)-hydroxy-3-(1-methylimidazol-2-yl)propylamide Iva-Phe-His(DNP)-1(S)-cyclohexylmethyl-2(R,S)-hydroxy-3-(1-methylimidazol-2-yl)propylamide with thiophenol to give the title compound in analogy to reference example 1(a).

$R_f$ (acetone/water 10:1)=0.05; MS (FAB): 620 (M+1).

(a)

Iva-Phe-His(DNP)-1(S)-cyclohexylmethyl-2(R,S)-hydroxy-3-(1-methylimidazol-2-yl)propylamide In analogy to reference example 1(b), 717 mg of Iva—Phe—His(DNP)—OH and 325 mg of 1(S)-cyclohexylmethyl-2(S)-hydroxy-3-(1-methylimidazol-2-yl)propylamine are coupled with pivaloyl chloride.

$R_f$ (acetonitrile/water 8:1)=0.11; MS (FAB): 786 (M+1).

(b)

1(S)-cyclohexylmethyl-2(R,S)-hydroxy-3-(1-methylimidazol-2-yl)propylamine 790 mg of 4(S)-cyclohexylmethyl-5(R,S)-(1-methylimidazol-2-yl-methyl)-1,3-oxazolidin-2-one are dissolved in 33 ml of 2N LiOH in MeOH/H$_2$O 1:1; and the solution is heated under reflux for 3 h, then diluted with 150 ml of water and extracted 3 times with 50 ml of CH$_2$Cl$_2$. Drying with Na$_2$SO$_4$ and concentration in vacuo results in the title compound as colorless oil which is used further without purification.

$R_f$(EA/MeOH)=0.11.

(c)

4(S)-Cyclohexylmethyl-5-(R,S)-(1-methylimidazol-2-yl-methyl)-1,3-oxazolidin-2-one 21.6 ml of 1.6M n-butyllithium solution in hexane are added dropwise, at −40° C., to 3.23 g of 1,2-dimethylimidazole dissolved in 70 ml of THF. After stirring at 0° C. for 40 min, 4.31 g of Z-cyclohexylalaninal (prepared as given in Synthesis 1983, 676), dissolved in 35 ml of THF, are added dropwise at −30° C. The reaction mixture is allowed to warm to R.T. and is stirred into 100 ml of saturated aqueous NaHCO$_3$ solution. The THF is removed in vacuo, and the aqueous phase is extracted 3 times with 100 ml of EA. Drying with Na$_2$SO$_4$ and concentration in vacuo is followed by chromatography on silica gel (MTB/MeOH 9:1) resulting in the title compound as a colorless oil.

$R_f$(MTB/MeOH 8:1)=0.17; MS (FAB): 278 (M+1).

The $^1$H NMR spectra measured at 270 MHz proved to be consistent with the structures indicated for all the title compounds.

The compounds of Examples 8–12 are prepared in analogy to Example 1.

EXAMPLE 8

Boc—Phe—His—ACHPA—Ile $\overset{R}{-}$ NH$_2$ $R_f$(EA/MeOH 1:1)=0.2; MS (FAB): 698 (M+1).

EXAMPLE 9

Iva—Thi—Cys(Me)—ACHPA—Ile $\overset{R}{-}$ NH$_2$ $R_f$(acetone/H$_2$O 10:1)=0.1; MS (FAB): 668 (M+1).

EXAMPLE 10

Ac—3-(1-Naphthyl)-alanyl-His—ACHPA—Ile $\overset{R}{-}$ NH$_2$ $R_f$(MeOH/H$_2$O 10:1)=0.1; MS (FAB): 690 (M+1).

EXAMPLE 11

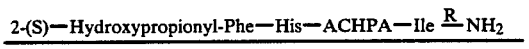

$R_f$(acetone/H$_2$O 5:1)=0.1; MS (FAB): 670 (M+1).

EXAMPLE 12

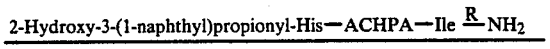

$R_f$(acetone/H$_2$O 5:1)=0.1; MS (FAB): 649 (M+1).
2-Hydroxy-3-(1-naphthyl)propionic acid can be prepared as given in J. agric. chem. Soc. Japan 19 (1943) 39, 43.

EXAMPLE 13

Etoc-Phe-His-1(S)-Cyclohexylmethyl-2(R,S)-hydroxy-3-(4,4-dimethyloxazolin-2-yl)propylamide 300 mg of Etoc-Phe-His(DNP)-1(S)-cyclohexylmethyl-2(R,S)-hydroxy-3-(4,4-dimethyloxazolin-2yl)-propylamide are reacted with thiophenol to give the title compound in analogy to reference example 1(a).

$R_f$ (acetonitrile/H$_2$O 10:1)=0.2; MS (FAB): 625 (M+1).

(a)
Etoc-Phe-His(DNP)-1(S)-cyclohexylmethyl-2(R,S)-hydroxy-3-(4,4-dimethyloxazolin-2-yl)propylamide 490 mg of Boc-His(DNP)-1(S)-cyclohexylmethyl-2(R,S)-hydroxy-3-(4,4-dimethyloxazolin-2-yl)propylamide are reacted with 169 mg of Etoc—Phe in analogy to Example 1(b).

$R_f$(EA/MeOH 10:1)=0.4; MS (FAB): 789 (M+1).

(b)
Boc-His(DNP)-1(S)-Cyclohexylmethyl-2(R,S)-hydroxy-3-(4,4-dimethyloxazolin-2-yl)propylamide 260 mg of Boc-1(S)-cyclohexylmethyl-2(R,S)-hydroxy-3-(4,4-dimethyloxazolin-2yl)propylamide are reacted with 299 mg of Boc—His(DNP)—OH in analogy to Examples 1(c) and 1(d).

$R_f$(EA)=0.3; MS (FAB): 670 (M+1).

(c)
Boc-1(S)-Cyclohexylmethyl-2(R,S)-hydroxy-3-(4,4-dimethyloxazolin-2-yl)propylamide 1.4 g of Boc-cyclohexylalaninal are reacted wih 1.4 ml of 2,4,4-trimethyloxazoline as stated by Meyers, J. Org. Chem. 39, 2778 (1974). 2 diastereomers in the ratio 1:1 are obtained.

D$_1$: $R_f$(MTB/diisopropyl ether 1:1)=0.15; MS: 369 (M+1).

D$_2$: $R_f$(MTB/diisopropyl ether 1:1)=0.10; MS: 369 (M+1).

D$_1$ is further processed for the preparation of the title compound in Example 13.

The compounds of Examples 14 and 15 are prepared in analogy to Example 13.

EXAMPLE 14

Etoc-Phe-His-1(S)-Cyclohexylmethyl-2(R,S)-hydroxy-3-(4(S,S)-sec.-butyl)oxazolin-2-yl)propylamide $R_f$ (acetonitrile/H$_2$O 10:1)=0.3; MS (FAB): 653 (M+1).

EXAMPLE 15

Iva-Thi-His-1(S)-Cyclohexylmethyl-2(R,S)-hydroxy-3-(4(S,S)-sec.-butyl-oxazolin-2-yl)propylamide $R_f$(acetonitrile/H$_2$O 10:1)=0.2; MS (FAB): 671 (M+1).

The oxazoline used in Examples 14 and 15 was obtained as follows:

(a) 4(S,S)-sec.-Butyl-2-methyloxazoline 15 g of 2-acetylamino-3-methylpentanol are dissolved in 200 ml of CH$_2$Cl$_2$ and, at 0° C. under argon, 3.5 ml of thionyl chloride are added dropwise, and the mixture is stirred at 0° C. for 3 h. The reaction solution is poured into 200 ml of saturated aqueous Na$_2$CO$_3$ solution, and the mixture is extracted 3 times with 100 ml of EA. Drying with Na$_2$SO$_4$ and concentration in vacuo results in the title compound plus bis(2-acetylamino-3-methylpentyl)sulfite, which can also be converted into the title compound by heating at 110° C. in toluene.

$R_f$(MTB/acetone 10:1)=0.3; MS: 142 (M+1).

(b) 2-Acetylamino-3-methylpentanol 22.4 g of Ac—Ile—OMe are dissolved in 200 ml of THF, 8.9 g of LiAlH$_4$ are added at 0° C., and the mixture is stirred at 0° C. for 1 h. About 90% of the THF is removed in vacuo, 100 ml of 5% strength aqueous KHSO$_4$ solution are added, and the mixture is extracted 3 times with 200 ml of EA. Drying over Na$_2$SO$_4$ and concentration in vacuo is followed by chromatography on silica gel (moblie phase MTB/acetone 10:1) resulting in the title compound as a colorless oil.

$R_f$(MTB/acetone 10:1)=0.1; MS: 160 (M+1).

EXAMPLE 16

Iva-Thi-His-1(S)-Cyclohexylmethyl-2(R,S)-hydroxy-4-(4(S,S)-sec.-butyloxazolin-2-yl)butylamide In analogy to reference examples 1(a) and 1(b), 260 mg of 1(S)-cyclohexylmethyl-2(R,S)-hydroxy-4-(4(S,S)-sec.-butyloxazolin-2-yl)butylamine are linked to the N-terminal dipeptide.

$R_f$ (acetonitrile/H$_2$O 10:1)=0.2; MS (FAB): 685 (M+1).

(a)
1(S)-Cyclohexylmethyl-2(R,S)-hydroxy-4-(4(S,S)-sec.-butyloxazolin-2-yl)butylamine In analogy to reference example (1c), 570 mg of 3-Boc-4(S)-cyclohexylmethyl-2,2-dimethyl-5(R,S)-[2-(4(S,S)-sec.-butyloxazolin-2-yl)ethyl]oxazolidine are deprotected and reacted further without purification.

(b)
3-Boc-4(S)-Cyclohexylmethyl-2,2-dimethyl-5(R,S)-[2-(4(S,S)-sec.-butyloxazolin-2-yl)ethyl]oxazolidine 3.76 g of 4(S,S)-sec.-butyl-2-methyloxazoline and 4.0 ml of N,N,N',N'-tetramethylethylenediamine are dissolved in 100 ml of THF and, at −78° C., added dropwise to 14.9 ml of a 1.6M solution of n-butyllithium in hexane are added dropwise. The mixture is stirred at this temperature for 30 min and then 1.15 g of 3-Boc-4(S)-cyclohexylmethyl-2,2-dimethyl-5(R,S)-iodomethyloxazolidine in 10 ml of THF are added dropwise. The reaction solution is stirred at R.T. for 1 h and is poured into 200 ml of saturated aqueous NaHCO$_3$ solution, and the mixture is extracted 3 times with 200 ml of EA. Drying over Na$_2$SO$_4$ and concentration in vacuo is followed by chromatography on silica gel (mobile phase MTB/diisopropyl ether 1:1). The title compound is obtained as a colorless oil.

$R_f$(MTB/diisopropyl ether 1:1)=0.6; MS (FAB): 451 (M+1).

(c) 3-Boc-4(S)-Cyclohexylmethyl-2,2-dimethyl-5(R,S)-iodomethyloxazolidine 2.4 g of Boc-2-cyclohexyl-1(S)-oxiran-2(R,S)-ylethylamine, 1.3 g of NaI and 1.1 ml of trimethylsilyl chloride are dissolved in 100 ml of acetonitrile, and the solution is stirred at R.T. for 1.5 h. Then 8.7 ml of a 1M solution of tetrabutylammonium fluoride in THF and 5.3 ml of dimethoxyethane are injected in. The mixture is stirred at R.T. for 2.5 h and then 200 ml of saturated aqueous NaHCO$_3$ solution are added, and the mixture is extracted 3 times with 200 l of MTB. Drying over Na$_2$SO$_4$ and concentration in vacuo is followed by chromatography on silica gel (mobile phase MTB/diisopropyl ether 1:2) resulting in the title compound as a colorless oil.

$R_f$ (MTB/diisopropyl ether 1:2)=0.5; MS: 422 (M—CH$_3$).

(d) Boc-2-Cyclohexyl-1(S)-oxiran-2(R,S)-ylethylamine 2.6 g of Boc-1(S)-cyclohexylmethylprop-2-en-1-ylamine are dissolved in 50 ml of CH$_2$Cl$_2$, and 1.9 g of m-chloroperbenzoic acid in 50 ml of CH$_2$Cl$_2$ are added dropwise at 0° C. The reaction solution is stirred at R.T. for 36 h and is then extracted first with 100 ml of 5% strength aqueous Na$_2$SO$_3$ solution and then with 100 ml of saturated aqueous Na$_2$CO$_3$ solution. Drying over Na$_2$SO$_4$ and concentration in vacuo are followed by chromatography on silica gel (mobile phase MTB/cyclohexane 1:1) resulting in the title compound as a colorless oil, diastereomer ratio 3:1 to 5:1.

Mixture of diastereomers:

$R_f$ (MTB/cyclohexane 1:1)=0.4; MS (FAB): 270 (M+1).

(e) Boc-1(S)-Cyclohexylmethylprop-2-en-1-ylamine 5.4 g of methyltriphenylphosphonium bromide are suspended in 100 ml of THF and, at R.T. under argon, 1.7 g of potassium t-butylate are added. The mixture is stirred at R.T. for 2 h, cooled to 0° C. and 3.9 g of Boc-cyclohexylalaninal in 50 ml of THF are added dropwise. The mixture is then stirred at 0° C. for 30 min, 100 ml of H$_2$O are added dropwise, and the THF is removed in vacuo. 100 ml of saturated aqueous NaHCO$_3$ solution are added, and the mixture is extracted 3 times with 100 ml of CH$_2$Cl$_2$. Drying over Na$_2$SO$_4$ and concentration in vacuo are followed by chromatography on silica gel (mobile phase MTB/cyclohexane 1:3) resulting in the title compound as a colorless oil.

$R_f$(MTB/cyclohexane 1:3)=0.4; MS: 254 (M+1).

The compounds of Examples 17–19 are prepared in analogy to Example 6.

EXAMPLE 17

Iva-Phe-His-1(S)-Cyclohexylmethyl-2(R,S)-hydroxy-3-(2-benzoxazolyl)propylamide $R_f$(EA/MeOH 5:1)=0.3; MS (FAB)=657 (M+1).

EXAMPLE 18

Iva-Phe-His-1(S)-Cyclohexylmethyl-2-hydroxy-3-(4-pyridyl)propylamide

1st diastereomer $R_f$(EA/MeOH 3:1)=0.2; MS (FAB)=617 (M+1).

EXAMPLE 19

Iva-Phe-His-1(S)-Cyclohexylmethyl-2-hydroxy-3-(4-pyridyl)propylamide

2nd diastereomer $R_f$(EA/MeOH 5:1)=0.1; MS (FAB)=617 (M+1).

EXAMPLE 20

Iva-Phe-His-1(S)-Cyclohexylmethyl-2(R,S)-hydroxy-3-aminopropylamide 100 mg of Iva-Phe-His-1(S)-cyclohexylmethyl-2(R,S)-hydroxy-3-benzyloxycarbonylaminopropylamide are hydrogenated in analogy to reference example 1.

$R_f$(MeOH)=0.1; MS=555 (M+1).

(a) Iva-Phe-His-1(S)-Cyclohexylmethyl-2(R,S)-hydroxy-3-benzyloxycarbonylaminopropylamide 250 mg of Iva-Phe-His(DNP)-1(S)-cyclohexylmethyl-2(R,S)-hydroxy-3-benzyloxycarbonylaminopropylamide are reacted with thiophenol in analogy to reference example 1(a).

$R_f$(EA/MeOH)=0.65; MS=689 (M+1).

(b) Iva-Phe-His(DNP)-1(S)-Cyclohexylmethyl-2(R,S)-hydroxy-3-benzyloxycarbonylaminopropylamide The title compound is prepared in analogy to reference example (1b) from 280 mg of Iva—Phe—His(DNP)—OH and 160 mg of 1(S)-cyclohexylmethyl-2(R,S)-hydroxy-3-benzyloxycarbonylaminopropylamine.

$R_f$(EA/MeOH 10:1)=0.5; MS (FAB)=855 (M+1).

(c) 1(S)-Cyclohexylmethyl-2(R,S)-hydroxy-3-benzyloxycarbonylaminopropylamine

The title compound is prepared in analogy to reference example (1c) from 220 mg of Boc-1(S)-cyclohexylmethyl-2(R,S)-hydroxy3benzyloxycarbonylaminopropylamine and is used "crude" for the next reaction step.

(d) Boc-1(S)-Cyclohexylmethyl-2(R,S)-hydroxy-3-benzyloxycarbonylaminopropylamine 1.3 g of Boc-1(S)-cyclohexylmethyl-2(R,S)-hydroxy-3-aminopropylamine are reacted with 1.3 g of Z—O—succinimide in analogy to Example (1g).

$R_f$(toluene/EA 2:1)=0.3; MS (FAB)=421 (M+1).

(e) Boc-1(S)-Cyclohexylmethyl-2(R,S)-hydroxy-3-aminopropylamine 1.4 g of Boc-1(S)-cyclohexylmethyl-2(R,S)-hydroxy-3-nitropropylamine are hydrogenated in 100 ml of ethanol/glacial acetic acid=10:1 over Raney nickel at 50° C. and under 50 bar for 6 h. The catalyst is filtered off with suction, and then the filtrate is concentrated, the residue is taken up in CH$_2$Cl$_2$, and the solution is washed twice with saturated Na$_2$CO$_3$ solution and once with saturated NaCl solution. The organic phase is dried with Na$_2$SO$_4$ and then evaporated, and the resulting oil is used in the next step without further purification.

R$_f$(MeOH)=0.3.

(f)
Boc-1(S)-Cyclohexylmethyl-2(R,S)-hydroxy-3-nitropropylamine 500 mg of Boc-cyclohexylalaninal and 25 mg of tetramethylguanidine (about 0.1 mole) are stirred in 10 ml of nitromethane at 0° C. for 16 h. The reaction solution is then concentrated and purified on silica gel using toluene/EA=4:1 s eluent.

R$_f$(toluene/EA 4:1)=0.25; MS=316.

EXAMPLE 21

Etoc—Thi—His-1(S)-Cyclohexylmethyl-2(R,S)-hydroxy-3-aminopropylamide is synthesized in analogy to Example 1.

EXAMPLE 22

Iva—Phe—His-1(S)-Cyclohexylmethyl-2(R,S)-hydroxy-4-(2-pyridyl)butylamide

The title compound is synthesized in analogy to reference example (1a) by reaction of 400 ml of Iva—Phe—His(DNP)-1(S)-cyclohexylmethyl-2(R,S)-hydroxy-4-(2-pyridyl)butylamide with thiophenol.

R$_f$(EA/MeOH 5:1)=0.15; MS (FAB)=631 (M+1).

(a)
Iva—Phe—His(DNP)-1(S)-Cyclohexylmethyl-2(R,S)-hydroxy-4-(2-pyridyl)butylamide The title compound is prepared in analogy to reference example (1b) and (1c) from 552 mg of Iva—Phe—His(DNP)—OH and 400 mg of Boc-1(S)-cyclohexylmethyl-2(R,S)-hydroxy-4-(2-pyridyl)butylamine.

R$_f$(EA/MeOH 10:1)=0.25; MS (FAB) 797 (M+1).

(b)
Boc-1(S)-Cyclohexylmethyl-2(R,S)-hydroxy-4-(2-pyridyl)butylamine

220 μl of 2-picoline (2 eq) are deprotonated in analogy to Example (6c). Then 300 mg of Boc-2-cyclohexyl-1(S)-oxiran-2(R,S)-ylethylamine in THF are added dropwise at −60° C. After 1 h, H$_2$O is added, and the mixture is extracted 3 times with EA. The organic phases are dried with Na$_2$so$_4$ and then concentrated, and the title compound is isolated by chromatography on SiO$_2$ with EA/H 2:1 as eluent.

R$_f$(EA/H 2:1)=0.3; MS (FAB)=363 (M+1).

EXAMPLE 23

Iva—Phe—His-1(S)-Cyclohexylmethyl-2(S)-hydroxy-5-(2-pyridyl)-pentylamide

The title compound is prepared in analogy to reference example (1a) by treatment of 110 mg of Iva—Phe—His(DNP)-1(S)-cyclohexylmethyl-2(S)-hydroxy-5-(2-pyridyl)pentylamide with thiophenol.

R$_f$ (acetonitrile/H$_2$O 8:1)=0.3; MS (FAB)=645 (M+1).

(a)
Iva—Phe—His(DNP)-1(S)-Cyclohexylmethyl-2(S)-hydroxy-5-(2-pyridyl)pentylamide The title compound is synthesized in analogy to reference example (1b) and (1c) from 263 mg of Iva—Phe—His(DNP)OH and 200 mg of 3-Boc-4(S)-cyclohexylmethyl-2,2-dimethyl-5-(3-(2-pyridyl)propyl)oxazolidine.

R$_f$(EA/MeOH)=0.4; MS (FAB)=811 (M+1).

(b)
3-Boc-4(S)-Cyclohexylmethyl-2,2-dimethyl-5-(3-(2-pyridyl)-propyl)oxazolidine 367 μl of 2-picoline are deprotonated in analogy to Example (6c). 500 mg of 3-Boc-4(S)-cyclohexylmethyl-2,2-dimethyl-5-(2-bromoethyl)oxazolidine in 10 ml of THF are added to the deep-red solution at −50° C. After 15 min, H$_2$O is added, and the mixture is extracted 3 times with EA. The organic phases are dried with Na$_2$SO$_4$ and then concentrated and chromatographed on silica gel (eluent: toluene/EA 3:1).

R$_f$(toluene/EA 3:1)=0.25; MS=417 (M+1).

(c)
3-Boc-4(S)-Cyclohexylmethyl-2,2-dimethyl-5-(2-bromoethyl)oxazolidine 1.6 ml of diethyl azodicarboxylate are added dropwise, at 20° C. under argon, to 690 mg of 3-Boc-4(S)-cyclohexylmethyl-2,2-dimethyl-5-(2-hydroxyethyl)oxazolidine, 2.6 g of triphenylphosphine and 1.6 g of pyridinium bromide in 15 ml of CH$_2$Cl$_2$. After 16 h at R.T., H$_2$O is added and the mixture is diluted with 100 ml of CH$_2$Cl$_2$. The organic phase is washed twice with saturated NaHCO$_3$ solution and once with saturated NaCl solution. The organic phase is dried with Na$_2$SO$_4$ and concentrated, and the residue is taken up in a little EA and filtered to remove PPh$_3$. Purification on silica gel provides the title compound (eluent: H/EA 15:1).

R$_f$(H/EA 15:1)=0.3; MS 404 (M).

(d)
3-Boc-4(S)-Cyclohexylmethyl-2,2-dimethyl-5-(2-hydroxymethyl)oxazolidine 10 g of Boc—ACHPA—OEt, 500 mg of p-toluenesulfonic acid and 7.2 ml of dimethoxypropane are heated at 80° C. in 160 ml of toluene under argon for 2 h. The mixture is then concentrated. The residue is added dropwise, at 0° C., to a suspension of 2 g of LiAlH$_4$ in 200 ml of THF. After 2.5 h at 0° C., 100 ml of 5% strength NaHSO$_4$ solution are added, and the mixture is extracted 3 times with EA. The combined organic phases are washed once with saturated NaHCO$_3$ solution. Drying with Na$_2$SO$_4$ is followed by concentration and chromatography (eluent: H/EA 2:1).

R$_f$(H/EA 4:1)=0.1; MS=342 (M+1).

Examples 24–27 are synthesized in analogy to Example 23.

EXAMPLE 24

Iva—Phe—His-1(S)-Cyclohexylmethyl-2(S)-hydroxy-5-(4-pyridyl)-pentylamide

R$_f$(acetonitrile/H$_2$O 10:1)=0.1; MS=644 (M).

EXAMPLE 25

Iva—Phe—His-1(S)-Cyclohexylmethyl-2(S)-hydroxy-5-(4(S,S)-sec.-butyloxazolin-2-yl)pentylamide $R_f$ (acetonitrile/H$_2$O 10:1)=0.1; MS (FAB)=693 (M+1).

EXAMPLE 26

Iva—Phe—His-1(S)-Cyclohexylmethyl-2(S)-hydroxy-5-(2-ethyl-4-pyridyl)pentylamide $R_f$ (CH$_2$Cl$_2$/MeOH/CH$_3$COOH/H$_2$O 80:20:1:1)=0.5;
MS (FAB): 673 (M+1).

EXAMPLE 27

Iva—Phe—His-1(S)-cyclohexylmethyl-2(S)-hydroxy-5-(4-ethyl-2-pyridyl)pentylamide $R_f$ (acetonitrile/H$_2$O 10:1)=0.3; MS (FAB): 673 (M+1).

EXAMPLE 28

Iva—Phe—His-1(S)-Cyclohexylmethyl-2(S)-hydroxy-5-(4-piperidinyl)-pentylamide

The title compound is prepared from Boc-1(S)-cyclohexylmethyl-2(S)-hydroxy-5-(4-benzyloxycarbonylpiperidinyl)pentylamide in analogy to reference example 1 and (1a)–(1c).

$R_f$ (acetonitrile/H$_2$O 2:1)=0.3; MS (FAB)=651 (M+1).

(a)
Boc-1(S)-Cyclohexylmethyl-2(S)-hydroxy-5(4-benzyloxycarbonylpiperidinyl)pentylamide 265 mg of 3-Boc-4(S)-cyclohexylmethyl-2,2-dimethyl-5-(3-(4-pyridyl)propyl)oxazolidine are hydrogenated on 40 mg of 5% rhodium on charcoal in 50 ml of ethanol at 100° C. and under 100 bar for 3.5 h. The catalyst is then filtered off, and the filtrate is concentrated. The residue is dissolved in 5 ml of DMF, 160 mg of Z—O—succinimide are added and the mixture is stirred at R.T. for 16 h. It is then concentrated and chromatographed on silica gel (eluent: H/EA 4:1).

$R_f$(H/EA)=0.4; MS=541 (M—CH$_3$).

EXAMPLE 29

Bis(1-Naphthylmethyl)acetyl-His-1(S)-cyclohexylmethyl-2(S)-hydroxy-5-(2-ethyl-4-pyridyl)pentylamide The title compound is prepared in analogy to reference example (1a) by treatment of bis(1-naphthylmethyl)acetyl-His(DNP)-1(S)-cyclohexylmethyl-2(S)-hydroxy-5-(2-ethyl-4-pyridyl)pentylamide with thiophenol:

$R_f$ (CH$_2$Cl$_2$/MeOH/CH$_3$COOH/H$_2$O 80:20:1:1)=0.6;
MS (FAB)=764 (M+1).

(a)
Bis-(1-Naphthylmethyl)acetyl-His(DNP)-1(S)-cyclohexylmethyl-2(S)-hydroxy-5-(2-ethyl-4-pyridyl)-pentylamide The title compound is synthesized in analogy to Example (1b) from bis(1-naphthylmethyl)acetic acid (prepared as given in Liebigs Ann. 468, 302) and Boc—His(DNP)-1(S)-cyclohexylmethyl-2(S)-hydroxy-5-(2-ethyl-4-pyridyl)pentylamide.

$R_f$(EA/MeOH 10:1)=0.5; MS (FAB)=930 (M+1).

(b)
Boc—His(DNP)-1(S)-Cyclohexylmethyl-2(S)-hydroxy-5-(2-ethyl-4-pyridyl)petnylamide The title compound is prepared in analogy to reference example (1b) from Boc—His(DNP)—OH and 1(S)-cyclohexylmethyl-2(S)-hydroxy-5-(2-ethyl-4-pyridyl)pentylamine, which is synthesized in analogy to reference example (1c) and Example (23b).

$R_f$(EA/MeOH 10:1)=0.3; MS (FAB)=708 (M+1).

The compounds of Examples 30 and 31 are prepared in analogy to Example 23.

EXAMPLE 30

Etoc—Phe—His-1(S)-Cyclohexylmethyl-2(S)-hydroxy-5-(4,4-dimethyloxazolin-2-yl)pentylamide $R_f$ (acetonitrile/H$_2$O 10:1)=0.1; MS (FAB): 653 (M+1).

EXAMPLE 31

Iva—Phe—His-1(S)-Cyclohexylmethyl-2(S)-hydroxy-5-(4,5-dimethyloxazol-2-yl)pentylamide $R_f$(EA/MeOH 5:1)=0.2; MS (FAB): 663 (M+1).

We claim:
1. A compound of the formula I

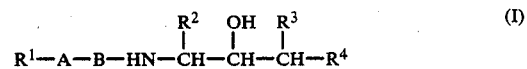

in which
R$^1$ denotes a radical of the formula II

in which W represents —CO—, —O—CO—, —SO$_2$— ior —NH—CO—, and R$^a$ represents hydrogen, (C$_1$-C$_{10}$)-alkyl which is saturated or singly or doubly unsaturated and which is unsubstituted or substituted by up to 3 identical or different radicals selected from the group consisting of hydroxyl, (C$_1$-C$_7$)-alkoxy, (C$_1$-C$_7$)-alkanoyloxy, carboxyl, (C$_1$-C$_7$)-alkoxycarbonyl, Cl, Br, amino, (C$_1$-C$_7$)-alkylamino, di-(C$_1$-C$_7$)-alkylamino, (C$_1$-C$_5$)-alkoxycarbonylamino, (C$_7$-C$_{15}$)-aralkoxycarbonyl-amino and 9-fluorenylmethoxycarbonylamino, or represents (C$_3$-C$_8$)-cycloalkyl, (C$_3$-C$_8$)-cycloalkyl-(C$_1$-C$_6$)-alkyl, (C$_6$-C$_{14}$)-aryl which is unsubstituted or substituted by one or two identical or different radicals selected from the group consisting of F, Cl, Br, I, hydroxyl, (C$_1$-C$_7$)-alkoxy, (C$_1$-C$_7$)-alkyl, (C$_1$-C$_7$)-alkoxycarbonyl, amino, anilino which is unsubstituted or substituted by up to 2 halogens, and trifluoromethyl, or represents (C$_6$-C$_{14}$)-aryl-(C$_1$-C$_6$)-alkyl in which the aryl moiety is unsubstituted or substituted by one or two identical or different radicals selected from the group consisting of F, Cl, Br, I, hydroxyl, (C$_1$-C$_7$)-alkoxy, (C$_1$-C$_7$)-alkyl, (C$_1$-C$_7$)-alkoxycarbonyl, amino, (C$_1$-C$_7$)-alkylamino, di-(C$_1$-C$_7$)-alkylamino, carboxyl, carboxymethoxy, amino(C$_1$-C$_7$)-alkyl, (C$_1$-C$_7$)-alkylamino-(C$_1$-C$_7$)-alkyl, di-(C$_1$-C$_7$)-alkylamino-(C$_1$-C$_7$)-alkyl, (C$_1$-C$_7$)-alkoxycarbonylmethoxy, carbamoyl, sulfamoyl, (C$_1$-C$_7$)-alkoxysulfonyl, sulfo- and guanidinomethyl, or represents the radical of a 5- or 6-membered monocyclic, or 9- or 10-membered bicyclic, heteroaromatic compound which has at least 1 carbon atom, 1–4 nitrogen atoms and/or 1 sulfur or oxygen atom, as ring members, and is unsubstituted or is mono-, di or trisubstituted independently by a member selected from the group of substitutents as defined for $(C_6-C_{14})$-aryl above, $R^4$ denotes a radical of the formula IV $$-X-(CH_2)_{n'}-R^7 \qquad (IV)$$

A denotes a radical, which is linked N-terminally with $R^1$ and C-terminally with B, of an amino acid selected from the group consisting of phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenyl-aalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, β-2-benzo(b)thienylalanine, β-3-benzo(b)thienylalanine, 2-fluorophenylalanine, 3-fluorophenylalanmine, 4-fluorophenylalanine, norleucine, cysteine, S-methylcysteine, 1,2,3,4-tetrahydroisoquinoline-3-carboxylic acid, homophenylalanine, DOPA, O-dimethyldopa, 2-amino-4-(2-thienyl)butyric acid, 2-amino-4-(3-thienyl)butyric acid, 3-(2-thienyl)serine, norvaline, (Z)-dehydrophenylalanine and (E)-dehydrophenylalanine, B denotes a radical of an amino acid as defined under A, $R^2$ denotes hydrogen, $(C_1-C_{10})$-alkyl, $(C_4-C_7)$-cycloalkyl, $(C_4-C_7)$-cycloalkyl-$(C_1-C_4)$-alkyl, $(C_6-C_{14})$-aryl or $(C_6-C_{14})$-aryl-$(C_1-C_4)$-alkyl, and $R^3$ denotes hydrogen, $(C_1-C_{10})$-alkyl, $(C_6-C_{14})$-aryl or $(C_6-C_{14})$-aryl-$(C_1-C_4)$-alkyl, X can be chosen to be absent or denotes O or S, n' can be 0, 1, 2, 3 or 4, with the proviso that n' is not 0 if $R^7$ is OH or NH, $R^7$ denotes hydrogen, OH, $NH_2$, or heteroaryl which can also be partially or completely hydrogenated or denotes a radical of the formula VI $$\overset{R^9}{\underset{|}{-CH}}-(CH_2)_p-Y-(CH_2)_q-R^{10} \qquad (VI)$$

$R^9$ representing hydrogen, $(C_1-C_7)$-alkyl, or $(C_1-C_7)$-alkyl which is monosubstituted by hydroxyl, $(C_1-C_3)$-alkoxy, $(C_1-C_5)$-alkylthio, carboxyl, $(C_1-C_5)$-alkoxycarbonyl, F, Cl, Br, I, $(C_1-C_5)$-alkylamino, di-$(C_1-C_5)$-alkylamino, $(C_1-C_5)$-alkoxycarbonylamino or $(C_7-C_{15})$-aralkoxycarbonylamino, $R^{10}$ denoting OH or $NH_2$, Y being absent or denoting $$\underset{|}{\overset{OH}{-CH-}},$$

p, q, independently of each other denoting 0, 1, 2, 3 or 4, and in the case where Y is $$\underset{|}{\overset{OH}{-CH,}}$$

q not being equal to 0, and heteroaryl denoting the radical of a heteroaromatic compound defined under $R^1$, and its physiologically tolerated salts.

2. A compound of the formula I as claimed in claim 1, in which $R^1$ denotes $(C_1-C_{11})$-alkanoyl, preferably n-decanoyl, formyl, acetyl, pivaloyl, isovaleryl or isobutyryl, optionally protected amino-$(C_1-C_{11})$-alkanoyl, preferably 4-aminobutyryl, 5-aminopentanoyl, 6-aminohexanoyl, 4-N-tert.-butoxycarbonylaminobutyryl, 5-N-tert.-butoxycarbonylaminopentanoyl or 6-N-tert.-butoxycarbonylaminohexanoyl, di-$(C_1-C_7)$-alkylamino-$(C_2-C_{11})$-alkanoyl, preferably dimethylaminoacetyl, $(C_4-C_9)$-cycloalkylcarbonyl, preferably cyclopropylcarbonyl, cyclobutylcarbonyl, cyclopentylcarbonyl or cyclohexylcarbonyl, $(C_6-C_{10})$-aryl-$(C_2-C_{11})$-alkanoyl, preferably phenylacetyl, phenylpropanoyl or phenylbutanoyl, 2-(2,6-dichloroanilino)phenylacetyl, 2-(N-benzyl-2,6-dichloroanilino)phenylacetyl, benzoyl which is optionally substituted by halogen, $(C_1-C_7)$-alkyl, $(C_1-C_7)$-alkoxy or $(C_1-C_7)$-alkoxycarbonyl, preferably 4-chlorobenzoyl, 4-methylbenzoyl, 2-methoxycarbonylbenzoyl or 4-methoxybenzoyl, 2-pyrrolylcarbonyl, 3-pyridylcarbonyl, benzenesulfonyl, $(C_1-C_{10})$-alkoxycarbonyl, preferably methoxycarbonyl, ethoxycarbonyl or tert.-butoxycarbonyl, $(C_1-C_{10})$-alkoxycarbonyl which is substituted by halogen, preferably 2,2,2-trichloroethoxycarbonyl or 1,1-dimethyl-2,2,2-trichloroethoxycarbonyl, $(C_6-C_{14})$-aryl-$(C_1-C_6)$-alkoxycarbonyl, preferably benzyloxycarbonyl or 9-fluorenylmethylcarbonyl and its physiologically tolerated salts.

3. A compound of the formula I as claimed in claim 1, in which $R^2$ denotes isobutyl, benzyl or cyclohexylmethyl, and its physiologically tolerated salts.

4. A compound of the formula I as claimed in claim 1, in which $R^3$ denotes hydrogen, isopropyl or isobutyl, and its physiologically tolerated salts.

5. A compound of the formula I as claimed in claim 1, in which $R^4$ is defined as in claim 1, $R^{10}$ denoting, however, $NH_2$ and its physiologically tolerated salts.

6. A compound of the formula I as claimed in claim 1, in which A and B are identical or different and denote phenylalanine, histidine, tyrosine, tryptophan, methionine, leucine, β-2-furylalanine, isoleucine, asparagine, aspartic acid, β-2-thienylalanine, β-3-thienylalanine, lysine, ornithine, valine, alanine, 2,4-diaminobutyric acid, arginine, 4-chlorphenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norleucine, norvaline, cysteine, S-methyl-cysteine, 1,2,3,4-tetrahydroisoquinoline-3-carboxylic acid, homophenylalanine, 2-amino-4-(2-thienyl)-butyric acid, (Z)-dehydrophenylalanine or (E)-dehydrophenylalanine and it physiologically tolerated salts.

7. A method for the treatment of high blood pressure, which comprises administration of an effective amount of a compound as claimed in claim 1, or its physiologically tolerated salt.

8. A pharmaceutical formulation for the treatment of high blood pressure, comprising an effective amount of a compound as claimed in claim 1, or its physiologically tolerated salt, and a pharmaceutically acceptable excipient.

* * * * *

UNITED STATES PATENT AND TRADEMARK OFFICE
CERTIFICATE OF CORRECTION

PATENT NO. : 4,855,286

DATED : August 8, 1989

INVENTOR(S) : ADALBERT WAGNER et al.

It is certified that error appears in the above-identified patent and that said Letters Patent is hereby corrected as shown below:

In claim 1, column 25, line 19, delete "chlorophenyl-aalanine" and substitute therefor --chlorophenyl-alanine--.

Signed and Sealed this

Seventeenth Day of July, 1990

Attest:

*Attesting Officer*

HARRY F. MANBECK, JR.

*Commissioner of Patents and Trademarks*